United States Patent
Blazevic

(10) Patent No.: US 9,316,597 B2
(45) Date of Patent: Apr. 19, 2016

(54) DETECTION OF SPURIOUS INFORMATION OR DEFECTS ON PLAYING CARD BACKS

(71) Applicant: Mladen Blazevic, New York, NY (US)

(72) Inventor: Mladen Blazevic, New York, NY (US)

( * ) Notice: Subject to any disclaimer, the term of this patent is extended or adjusted under 35 U.S.C. 154(b) by 294 days.

(21) Appl. No.: 13/899,768

(22) Filed: May 22, 2013

(65) Prior Publication Data

US 2014/0347471 A1  Nov. 27, 2014

(51) Int. Cl.
  H04N 7/18  (2006.01)
  G01N 21/88  (2006.01)
  G01N 21/95  (2006.01)
  H04N 5/33  (2006.01)
  A63F 1/12  (2006.01)
  A63F 1/14  (2006.01)
  A63F 9/24  (2006.01)

(52) U.S. Cl.
  CPC .............. *G01N 21/8806* (2013.01); *A63F 1/12* (2013.01); *A63F 1/14* (2013.01); *G01N 21/95* (2013.01); *H04N 5/33* (2013.01); *H04N 5/332* (2013.01); *A63F 2009/2445* (2013.01); *G01N 2021/8816* (2013.01); *G01N 2021/8845* (2013.01); *G01N 2201/0221* (2013.01)

(58) Field of Classification Search
  None
  See application file for complete search history.

(56) References Cited

U.S. PATENT DOCUMENTS

| | | | |
|---|---|---|---|
| 4,531,187 A | 7/1985 | Uhland | |
| 5,169,155 A * | 12/1992 | Soules et al. | 273/293 |
| 5,605,334 A | 2/1997 | McCrea, Jr. | |
| 5,722,893 A | 3/1998 | Hill | |
| 5,770,533 A | 6/1998 | Franchi | |
| 5,941,769 A | 8/1999 | Order | |
| 6,039,650 A | 3/2000 | Hill | |
| 6,093,103 A | 7/2000 | McCrea, Jr. | |
| 6,117,012 A | 9/2000 | McCrea, Jr. | |
| 6,403,908 B2 | 6/2002 | Stardust et al. | |
| 6,460,848 B1 | 10/2002 | Soltys et al. | |
| 6,517,435 B2 | 2/2003 | Soltys | |
| 6,517,436 B2 | 2/2003 | Soltys et al. | |
| 6,520,857 B2 | 2/2003 | Soltys et al. | |
| 6,527,191 B1 | 3/2003 | Jannersten | |
| 6,527,271 B2 | 3/2003 | Soltys et al. | |
| 6,530,836 B2 | 3/2003 | Soltys et al. | |
| 6,530,837 B2 | 3/2003 | Soltys et al. | |
| 6,533,276 B2 | 3/2003 | Soltys et al. | |
| 6,533,662 B2 | 3/2003 | Soltys et al. | |
| 6,579,180 B2 | 6/2003 | Soltys et al. | |

(Continued)

FOREIGN PATENT DOCUMENTS

WO  WO/00/51076  8/2000

*Primary Examiner* — Christopher S Kelley
*Assistant Examiner* — Christopher Findley
(74) *Attorney, Agent, or Firm* — Mark A. Litman & Associates, P.A.

(57) ABSTRACT

Methods and systems detect markings or flaws on the backs of playing cards. The method includes: providing ambient radiation at a gaming table and reflecting some of that radiation off a back surface of a playing card; capturing reflected radiation with a radiation sensor; the radiation sensor transmitting signals based on the reflected radiation captured by the radiation sensor; the transmitted signals providing data that contains image data of the back of the playing card; and displaying an image of the back of the playing card based on the image data. The transmitted signals provide image data of the back of the playing card and are also received by a processor that evaluates or compares that data. The system may be an installed casino system (with eye-in-the-sky technology), a portable box, or a component within a shuffling device or dealer shoe.

20 Claims, 1 Drawing Sheet

(56) References Cited

U.S. PATENT DOCUMENTS

| | | |
|---|---|---|
| 6,579,181 B2 | 6/2003 | Soltys et al. |
| 6,582,301 B2 | 6/2003 | Hill |
| 6,588,750 B1 | 7/2003 | Scheper et al. |
| 6,595,857 B2 | 7/2003 | Soltys et al. |
| 6,629,894 B1 | 10/2003 | Purton |
| 6,638,161 B2 | 10/2003 | Soltys et al. |
| 6,651,981 B2 | 11/2003 | Grauzer et al. |
| 6,651,982 B2 | 11/2003 | Grauzer et al. |
| 6,652,379 B2 | 11/2003 | Soltys et al. |
| 6,655,684 B2 | 12/2003 | Grauzer et al. |
| 6,659,461 B2 | 12/2003 | Yoseloff |
| 6,663,490 B2 | 12/2003 | Soltys et al. |
| 6,676,127 B2 | 1/2004 | Johnson |
| 6,685,568 B2 | 2/2004 | Soltys et al. |
| 6,688,979 B2 | 2/2004 | Soltys et al. |
| 6,712,696 B2 | 3/2004 | Soltys et al. |
| 6,726,205 B1 | 4/2004 | Purton |
| 7,338,044 B2 | 3/2008 | Grauzer et al. |
| 7,367,561 B2 | 5/2008 | Blaha et al. |
| 7,367,884 B2 | 5/2008 | Breeding et al. |
| 7,374,170 B2 | 5/2008 | Grauzer et al. |
| 7,384,044 B2 | 6/2008 | Grauzer et al. |
| 7,407,438 B2 | 8/2008 | Schubert et al. |
| 7,413,191 B2 | 8/2008 | Grauzer et al. |
| 7,434,805 B2 | 10/2008 | Grauzer et al. |
| 7,584,962 B2 | 9/2009 | Breeding et al. |
| 7,584,963 B2 | 9/2009 | Krenn et al. |
| 7,593,544 B2 | 9/2009 | Downs, III et al. |
| 7,594,660 B2 | 9/2009 | Baker et al. |
| 7,597,623 B2 | 10/2009 | Grauzer et al. |
| 7,669,852 B2 | 3/2010 | Baker et al. |
| 7,677,565 B2 | 3/2010 | Grauzer et al. |
| 7,677,566 B2 | 3/2010 | Krenn et al. |
| 7,699,694 B2 | 4/2010 | Hill |
| 7,717,427 B2 | 5/2010 | Grauzer et al. |
| 7,753,373 B2 | 7/2010 | Grauzer et al. |
| 7,764,836 B2 * | 7/2010 | Downs, III ............... A63F 1/12 273/149 R |
| 7,769,232 B2 | 8/2010 | Downs, III |
| 7,784,790 B2 | 8/2010 | Grauzer et al. |
| 7,854,430 B2 | 12/2010 | Toyama |
| 7,933,444 B2 | 4/2011 | Downs, III et al. |
| 7,933,448 B2 | 4/2011 | Downs, III |
| 7,946,586 B2 | 5/2011 | Krenn et al. |
| 7,950,663 B2 | 5/2011 | Schubert et al. |
| 7,967,294 B2 | 6/2011 | Blaha et al. |
| 7,967,672 B2 | 6/2011 | Shigeta |
| 7,971,881 B2 | 7/2011 | Toyama et al. |
| 7,976,023 B1 | 7/2011 | Hessing et al. |
| 7,988,152 B2 | 8/2011 | Sines |
| 8,002,638 B2 | 8/2011 | Grauzer et al. |
| 8,011,661 B2 | 9/2011 | Stasson |
| 8,012,029 B2 | 9/2011 | Johnson |
| 8,020,869 B2 | 9/2011 | Kaji et al. |
| 8,025,294 B2 | 9/2011 | Grauzer et al. |
| 8,038,521 B2 | 10/2011 | Grauzer et al. |
| RE42,944 E | 11/2011 | Blaha et al. |
| 8,070,574 B2 | 12/2011 | Grauzer et al. |
| 8,109,514 B2 | 2/2012 | Toyama |
| 8,118,305 B2 | 2/2012 | Grauzer et al. |
| 8,150,875 B1 | 4/2012 | Dubrovsky et al. |
| 8,170,323 B2 | 5/2012 | Downs, III et al. |
| 8,191,894 B2 | 6/2012 | Grauzer et al. |
| 8,205,884 B2 | 6/2012 | Schubert et al. |
| 8,210,535 B2 | 7/2012 | Grauzer et al. |
| 8,210,536 B2 | 7/2012 | Blaha |
| 8,221,244 B2 | 7/2012 | French |
| 2004/0026636 A1 | 2/2004 | Shigeta |
| 2005/0156046 A1 * | 7/2005 | Goldenberg ............ G06K 7/10 235/462.13 |
| 2005/0242500 A1 | 11/2005 | Downs |
| 2007/0018389 A1 | 1/2007 | Downs |
| 2007/0102879 A1 | 5/2007 | Stasson |
| 2009/0291758 A1 | 11/2009 | Moretti |
| 2010/0019449 A1 | 1/2010 | Downs, III et al. |
| 2010/0061342 A1 | 3/2010 | Frederiks et al. |
| 2011/0020175 A1 | 1/2011 | Collard et al. |
| 2011/0227283 A1 | 9/2011 | Schubert |
| 2013/0343599 A1 * | 12/2013 | Lee ....................... G06K 9/2063 382/100 |

* cited by examiner

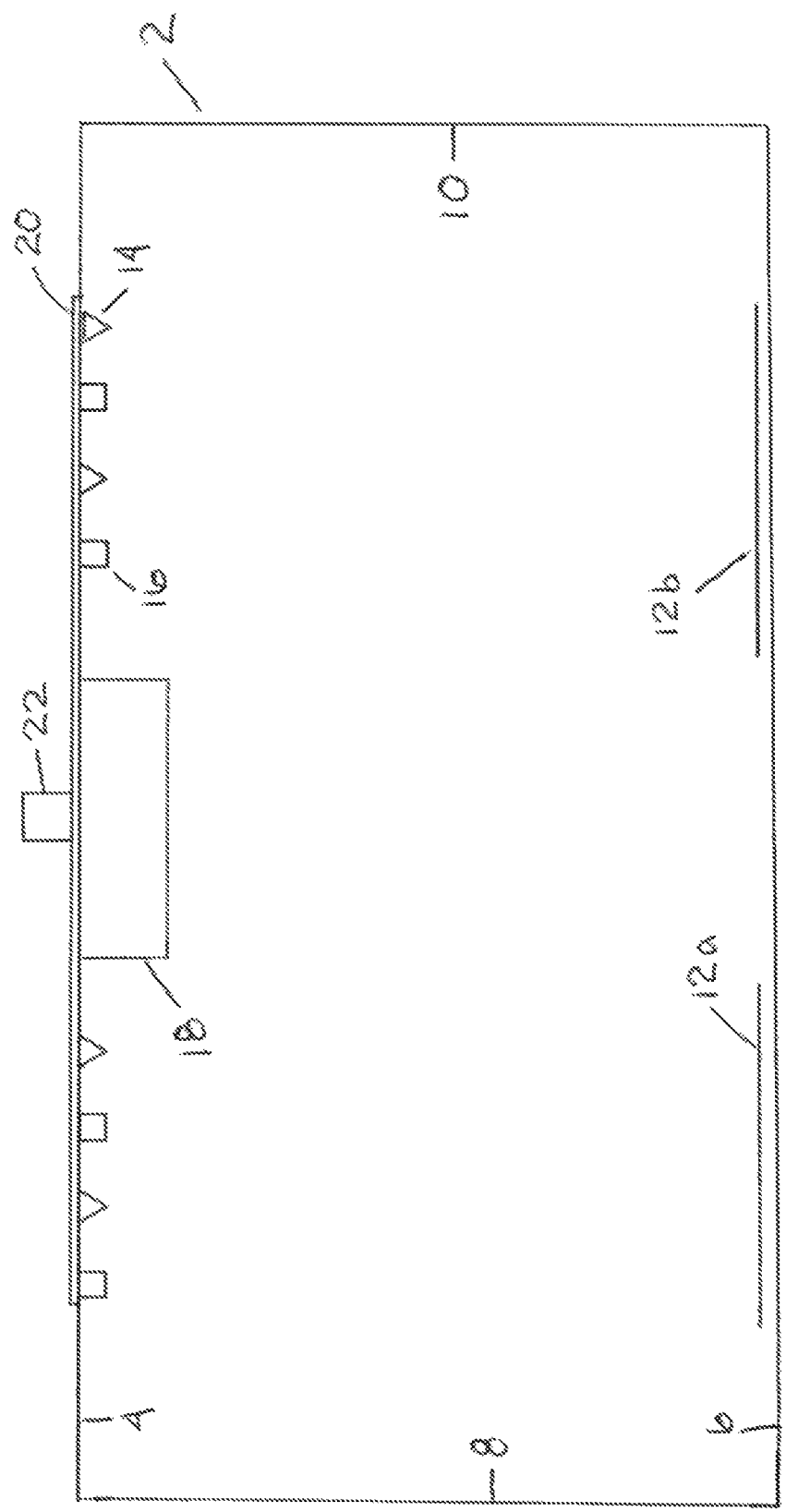

DETECTION OF SPURIOUS INFORMATION OR DEFECTS ON PLAYING CARD BACKS

BACKGROUND OF THE INVENTION

1. Field of the Invention

The present invention relates to the field of playing cards, particularly playing cards used in wagering games, and more particularly the security of playing cards with respect to spurious information and defects in the back surfaces of playing cards.

2. Background of the Art

Even with the highly electronic advances that have occurred within the gaming industry, playing cards, dice and other physical gaming objects are still important implements within gaming venues. Playing cards in particular are suspect of and capable of manipulation by players because of the intimate and repeated contact of the playing cards by the players.

Card games and card tournaments can involve millions of dollars in individual and total prizes. Some players have attempted to mark playing cards on the backs or edges of cards so that the markings enable them to identify the suit and rank of cards without having the faces of the cards exposed. This provides a significant advantage to players versus other players or the house. Even though marking has been going on for over a hundred years, and even though cards are visually inspected by dealers and automated systems can inspect cards, newer techniques and more sophisticated markings or defects can still go undetected. New types of markings are invisible to the naked eye, but can be clearly seen with the help of specially made contact lenses and glasses and small portable cameras with built in video transmitters. Small CPUs in pockets transfer the information to the player via wireless, inductive earphone. The marked cards (packaged in original boxes and sealed), chemicals and cheating devices are being widely sold over Internet for the last couple of years. As recently as May 2013, an international professional poker player was accused of cheating (and winning over 10 million dollars) in a major tournament by reading variations in printed patterns on the backs of playing cards. This is asserted to have occurred in spite of the casino supplying and controlling the cards, regular change of decks of cards, and constant dealer examination of the cards.

The types of markings that can be provided on backs and sides of playing cards include at least, visible ink, invisible (e.g., infrared and/or ultraviolet reflecting ink), solvents that smear existing inks, abrading or cutting marks, matting agents that alter reflectivity of surfaces, bending or curling of cards, and the like, alone or in combinations. Manual inspection can be done visually (with or without red color glasses that enhance viewability of the one part of the visible spectrum, but markings in infrared or UV can't be detected with naked eye), manually (feeling for abrasions or marks) and by combinations of these actions.

Many different types of automated reading, sensing and optical electrical or electromechanical systems are known for use in reading or sensing playing cards. A non-limiting sampling of those types of systems is reviewed below.

U.S. Pat. No. 6,403,908 (Stardust) discloses an automated method and apparatus for sequencing and/or inspecting decks of playing. The method and apparatus utilizes pattern recognition technology or other image comparison technology to compare one or more images of a card with memory containing known good images of a complete deck of playing cards to identify each card as it passes through the apparatus. Once the card is identified, it is temporarily stored in a location corresponding to or identified according to its position in a properly sequenced deck of playing cards. Once a full set of cards has been stored, the cards are released in proper sequence to a completed deck hopper. The method and apparatus also includes an operator interface capable of displaying a magnified version of potential defects or problem areas contained on a card which then may be viewed by the operator on a monitor or screen and either accepted or rejected via operator input. The present invention is also capable of providing an overall wear rating for each deck of playing cards. In order to certify that deck of playing cards is good and acceptable for play, the casino must ascertain that: (1) there is one and only one of each type (i.e. by suit and rank) of playing card in the deck of playing cards, (2) all of the backs of the playing cards contained in the deck are of the same color, (3) there are no defective playing cards (i.e. torn or cracked cards, cards with dimples or fingernail marks, cards with missing print or cards with spots), and (4) there are no boxed cards (cards facing backwards, etc.) contained in the deck of playing cards. Imaging cameras are used to obtain one or more images of each side of the card after the double card check is made. A low resolution is made of the front to determine suit and rank and back to determine color of the card. Generally, high resolution imaging is utilized to determine fine marks and problems. If the system is not in an inspect mode, it is possible to use the cameras simply to image a corner of the card, since the information necessary as to color and suit and rank is available in this portion of each card.

U.S. Pat. No. 5,941,769 (Order) discloses that in professional use in table games of chance with playing cards are provided which will register and evaluate all phases of the run of the game automatically. This is achieved by a card shoe with an integrated device for recognition of the value of the drawn cards (optical recognition device and mirroring into a CCD-image converter); photodiodes arranged under the table cloth to register separately the casino light passing through each area for placing the gaming chips and areas for placing the playing cards in dependence of the arrangement or movement of the chips and playing cards on the mentioned areas; a device for automatic recognition of each bet (scanner or a RFID-system comprising a S/R station and gaming objects with integrated transponder); an EDP program created in accordance with the gaming rules to evaluate and store all data transmitted from the functional devices to the computer; and a monitor to display the run of the game and players' wins.

U.S. Pat. No. 5,770,533 (Franchi) describes a casino operating system for controlling the flow of funds and monitoring gambling activities in a casino or a gaming establishment utilizing a network of computers, including a central computer and individual game computers. Each player receives an encoded betting card from the cashier. At the games, each player position is equipped with a control panel including a card reader into which the betting card is inserted. The control panel also includes an electronic screen and keyboard. From the control panel, the player may place a bet and perform all options available to the player in the particular game. The system records the hands dealt to each player and the winner, and credits or debits the player's betting card accordingly. In an alternative embodiment, the casino operating system allows the players to use chips to place bets instead of the above-described betting card. The chips are marked or encoded so that they can be counted once final bets have been placed to determine the amount of each player's bet. In games requiring the placement of bets in certain positions on the gaming table, each player may be provided with a betting marker used to indicate the position of his bets on the table, a touch-sensitive screen maybe used whereby bets are placed by touching the desired position on the screen, or a two-way remote control console for placing bets. The casino operating system is an open architecture system adaptable to accommodate the differing needs of each casino.

U.S. Pat. No. 4,531,187 (Uhland) describes a system for monitoring the play at gambling games is disclosed. The preferred embodiment comprises a system for monitoring the play at blackjack as that game is played in casinos. The system typically will comprise video monitor means for generating a digital representation of the bets made by the players and of the cards dealt to the players and to the dealer, so that an output can be generated indicating whether the correct payouts are made and bets collected. An alarm signal is generated if an error is made in the play of the game. An alarm signal may also be generated if the long-term statistics of the game indicate that the odds ordinarily applicable to the game have been departed from over a period of time.

U.S. Pat. No. 8,221,244 (French) describes methods and systems for intelligent tracking and/or play and/or management of card gaming use an intelligent card distribution or holding device with detectors for determining the value and unique identity of individual cards and for recording card play. Playing cards are equipped with a read/write data storage connected to a transponder and/or incorporated into electromagnetic writable particles or smart particles (smart dust). A system of the invention records various game play events on the playing cards themselves during game play and optionally also in a database on the system. In specific embodiments, the principal scanning and writing elements and electronic and optical interfaces are embodied into a hand-held card holder (HHCH). The system can scan playing cards, scan gaming chips, indicate a player's win/loss/draw, increase or decrease player betting positions, and compute awards to players based on their playing activity.

U.S. Pat. No. 7,967,672 (Shigeta) describes a card reading device that comprises a rail for guiding a card; card sensors for detecting a passing card which is slid by hand and guided by the rail, which are placed in a card sliding direction with a certain gap; and reading sensors for reading code attached to the card, which are placed between the two card sensors in the card sliding direction. The card have the code which is printed in UV-luminous ink on the card, and the code comprises at least two code rows which are placed across the card sliding direction with a certain gap. The two reading sensors are placed in positions which correspond to the gap of the two code rows, and the card sensors output signal for detecting a position of the passing card.

U.S. Pat. No. 6,629,894 (Purton) describes a card inspection device that includes a first loading area adapted to receive one or more decks of playing cards. A drive roller is located adjacent the loading area and positioned to impinge on a card if a card were present in the loading area. The loading area has an exit through which cards are urged, one at a time, by a feed roller. A transport path extends from the loading area exit to a card accumulation area. The transport path is further defined by two pairs of transport rollers, one roller of each pair above the transport path and one roller of each pair below the transport path. A camera is located between the two pairs of transport rollers, and a processor governs the operation of a digital camera and the rollers. A printer produces a record of the device's operation based on an output of the processor, and a portion of the transport path is illuminated by one or more blue LEDs. Preferably a low temperature source of light is located so as to illuminate the area of the card that is being scanned.

The computer or signal processor compiles the scan data and reports and records the result of the scans of all of the cards in the one or more decks. FIG. 15 illustrates how a card transport path 400 may be subdivided by locating baffles above or below the roller pairs in order to create distinct zones. Each zone may have a particular form of detector, polarimeter, diode or line scanner as well as a particular light source or lighting method. By locating sensors both above and below the transport path, both sides of the card may be examined simultaneously. This provides the opportunity to detect suit and value of an inverted card as well as increasing the sophistication with which tampering may be detected. Polarized light may be used to detect certain forms of tampering. In such a case, the polarity of the light source may be rotated during the detection process. Similarly, a non-polarized source may be moved during the detection process to create a moving shadow. One or more light sources may be movable or set to illuminate off-axis so that certain forms of scratches and pinholes may be more easily detected by their shadow or reflectance. It is contemplated that both color and monochrome imaging methods may provide useful information about the condition of the cards. Similarly both digital and analogue sensing methods are seen to have independent utility and functionality with regard to both suit and value detection as well as the detection of faults, wear and tampering. It should be noted that the compartmentalization of the card transport path into distinct lighting and sensing zones may be applied to any embodiment disclosed.

Published U.S. Patent Application Document No. 20050242500 (Downs III) describes a sensing system for determining the rank and suit of playing cards. The system includes a sensing module capable of reading a line of data from a printed image, a position sensor and a hardware component that combines the signals from the sensing module and position sensor, converts the signal to binary values and compares the converted signal to stored signals. The comparisons are correlated to identify card rank and Suit. The system can be used in a playing card delivery shoe used to control the game of baccarat. The shoe may be a customary dealing shoe equipped with a sensing module, or may be a mechanized shoe. The mechanized shoe may comprise a) an area for receiving a first set of playing cards useful in the play of the casino table card game of baccarat; b) first card mover that moves playing cards from the first set to a playing card staging area wherein at least one playing card is staged in an order by which playing cards are removed from the first set of and moved to the playing card staging area; c) second playing card mover that moves playing cards from the playing card staging area to a delivery area wherein playing cards removed from the staging area to the delivery shoe are moved in the same order by which playing cards were removed from the first set of playing cards and moved to the playing card staging area; and d) playing card reading sensors that read at least one playing card value of each playing card separately after each playing card has been removed from the area for receiving the first set of playing cards and before removal from the playing card delivery area One exemplary sensing system is a CIS line scanning system with an associated card position sensor and a FPGA hardware element.

Published U.S. Patent Application Document No. 20070018389 (Downs III) describes a method and an apparatus determines at least one of rank or suit of a playing card. The apparatus has at least one two-dimensional complementary metal oxide semiconductor imaging system that provides a signal when playing cards are moved over the system. The signal is a series of gray scale values that are converted into binary values. The sensed data is transmitted to a hardware component that identifies at least one of rank and suit to an external data storage device.

Published U.S. Patent Application Document No. 20070102879 (Stasson) describes a playing card shuffling device has a visual display in information communication with the playing card shuffling device. At least one processor is programmed to provide displayable information to the visual display indicative of an amount of time remaining or time expired in a procedure performed by the shuffling device. FIG. 1 shows a partial perspective view of the top surface of a first shuffling and card verification apparatus according to a practice of the invention. In this example of the invention, the device randomizes and/or verifies one or two decks of cards. The shuffling apparatus has a card accepting/receiving area that is preferably provided with a stationary lower support surface that slopes downwardly from the nearest outer side of the shuffling and verifying apparatus. A depression is provided in that nearest outer side to facilitate an operator's ability to place or remove cards into the card accepting/receiving area. The top surface of the shuffling and verifying apparatus is provided with a visual display (e.g., LED, liquid crystal, micro monitor, semiconductor display, multi-segment display, etc.), and a series of buttons, touch pads, lights and/or displays. These elements on the top surface of the shuffling and verifying device may act to indicate power availability (on/off), shuffler state (jam, active shuffling, completed shuffling cycle, insufficient numbers of cards, missing cards, sufficient numbers of cards, complete deck(s), damaged or marked cards, entry functions for the dealer to identify the number of players, the number of cards per hand, access to fixed programming for various games, the number of decks being shuffled, card calibration information, mode of operation (i.e. shuffling, verifying or both shuffling and verifying) and the like), or other information useful to the operator or casino. Among the non-limiting examples of these techniques are 1) a sensor so that when a pre-selected portion of the card (e.g., leading edge, trailing edge, and mark or feature on the card) passes a reading device, such as an optical reader, the bottom pick-off roller is directed to disengage, revolve freely, or withdraw from the bottom of the set of cards; 2) the first set of nip rollers or off-set rollers may have a surface speed that is greater than the surface speed of the bottom pick-off roller, so that engagement of a card applies tension against the bottom pick-off roller and the roller disengages with free rolling gearing, so that no forward moving forces are applied to the first card or any other card exposed upon movement of the first card; 3) a timing sequence so that, upon movement of the bottom pick-off roller for a defined period of time or for a defined amount of rotation (which correlates into a defined distance of movement of the first card), the bottom pick-off roller disengages, withdraws, or otherwise stops applying forces against the first card and thereby avoids applying forces against any other cards exposed by movement of the first card from the card accepting/receiving area 106 and 4) providing a stepped surface (not shown) between pick-off roller and off-set rollers 146 that contacts a leading edge of each card and will cause a card to be held up or retained in the event that more than one card feeds at a time.

Shuffler systems, especially those having a scanning system, can be converted to card inspections systems or may have card inspection systems according to the present technology integrated into the shufflers, randomizers and playing card delivery systems. Examples of such card moving systems include, but are not limited to U.S. Pat. Nos. 8,210,536; 8,210,535; 8,205,884; 8,191,894; 8,170,323; 8,150,875; 8,118,305; 8,109,514; 8,070,574; RE 42,944; U.S. Pat. Nos. 8,038,521; 8,025,294; 8,012,029; 8,011,661; 8,002,638; 7,988,152; 7,976,023; 7,971,881; 7,967,294; 7,950,663; 7,946,586; 7,933,448; 7,933,444; 7,854,430; 7,784,790; 7,769,232; 7,764,836; 7,753,373; 7,717,427; 7,699,694; 7,677,566; 7,677,565; 7,669,852; 7,597,623; 7,594,660; 7,593,544; 7,584,963; 7,584,962; 7,434,805; 7,413,191; 7,407,438; 7,384,044; 7,374,170; 7,367,884; 7,367,561; 7,338,044; 6,676,127; 6,659,461; 6,655,684; 6,651,982; 6,651,981; 6,588,750; and 6,588,750.

Other disclosures have also contemplated optically reading of playing cards. For example, U.S. Pat. Nos. 6,582,301; 6,039,650; and 5,722,893 to Hill et al. describes a shoe with a card scanner, which optically scans a playing card as the card moves out of shoe. The card suit and value is then recognized by a neural-network algorithm. Other disclosures have also attempted to track cards by use of card shoes that optically recognize the cards as they are drawn from the shoe. For example, U.S. Pat. Nos. 5,941,769 and 6,460,848 disclose a card shoe with an optical device that deflects and transmits a reflected image of the card value imprint from the drawn playing card to a CCD image converter. Still other disclosures have attempted to combine detection of playing cards optically and gambling chips by some means. For example, U.S. Pat. Nos. 5,605,334; 6,093,103 and 6,117,012 to McCrea et al., disclose a game table system for monitoring each hand in a progressive live card game. The system comprises a shoe that optically detects the value and suit of each card, a game bet sensor to detect the presence or absence of a bet, a card sensor located at each player position to detect the presence or absence of a playing card, and a game control. The game control receives information on the presence or absence of a bet or playing card to ensure a bet is placed before the playing card is dealt.

Published U.S. Patent Application Document No. 20100019449 (Downs III) describes how a playing card delivery shoe is used in the play of the casino table card game of baccarat or blackjack or any game where cards are pulled one at a time from the shoe. The apparatus comprises a reader or an imager that scans lines bisecting the image at spaced intervals. The scanning occurs on playing cards in at least the region where suit and rank symbols are provided. The scanner output is a series of voltages that are converted to binary information. This binary information is compared to stored binary information to determine rank and suit. The upper surface of the output end of the shoe contains a partial barrier for cards being scanned. The partial barrier has an elevated surface and limits a size of a pathway so that only one card can be removed at a time.

U.S. Pat. No. 6,460,848 (Soltys) describes a system that automatically monitors playing and wagering of a game, including the gaming habits of players and the performance of employees. A card deck reader automatically reads a symbol from each card in a deck of cards before a first one of the cards is removed. The symbol identifies a respective rank and suit of the card. There are numerous other related patents including U.S. Pat. Nos. 6,712,696; 6,688,979; 6,685,568; 6,663,490; 6,652,379; 6,638,161; 6,595,857; 6,579,181; 6,579,180; 6,533,662; 6,533,276; 6,530,837; 6,530,836; 6,527,271; 6,520,857; 6,517,436; and 6,517,435.

Other systems known to be available for reading of card symbols (e.g., suits and rank) include at least WIPO Published Application WO/2000/051076 (Dolphin); Published U.S. Patent Application Documents No. 2011020175; 2010061342; 20040026636; and U.S. Pat. Nos. 6,726,205; 6,527,191; 6,533,276 and 8,020,869. All of the references cited herein are incorporated by reference in their entirety to provide enabling background for systems and technology and methods.

SUMMARY OF THE INVENTION

The present invention relates to the field of methods and systems for detection of markings or flaws on the backs of playing cards. The invention includes a method and system for detecting errors in the back of playing cards. The method includes: providing ambient infrared radiation at a gaming table and reflecting at least some of that infrared radiation off a back surface of a playing card; capturing reflected infrared radiation with an infrared radiation sensor; the infrared radiation sensor transmitting signals based on the reflected infrared radiation captured by the infrared radiation sensor; the transmitted signals providing data that contains image data of the back of the playing card; and displaying an image of the back of the playing card based on the image data. The transmitted signals provide data that contains image data of the back of the playing card and is also received by a processor that compares that transmitted data with reference data of a standard playing card back. The system may be an installed casino system (with eye-in-the-sky technology), a portable box, or a component within a shuffling device or dealer shoe.

BRIEF DESCRIPTION OF THE FIGURES

FIG. 1 shows a full frontal view of a device according to the present technology.

DETAILED DESCRIPTION OF THE INVENTION

The present invention relates to the field of methods and systems for detection of markings or flaws on the backs or edges of playing cards. The invention includes a method for detecting errors in the back of playing cards. The method includes: providing ambient infrared radiation at a gaming table and reflecting at least some of that infrared radiation off a back surface of a playing card; capturing reflected infrared radiation with an infrared radiation sensor; the infrared radiation sensor transmitting signals based on the reflected infrared radiation captured by the infrared radiation sensor; the transmitted signals providing data that contains image data of the back of the playing card; and displaying an image of the back of the playing card based on the image data. The transmitted signals provide data that contains image data of the back of the playing card is also received by a processor that compares that transmitted data with reference data of a standard playing card back. The differences between the image of the back of the playing card based on the image data and the reference data are either a) highlighted in a visual display or b) the processor identifying a degree of difference between the image of the back of the playing card based on the image data and the reference data. The degree of differences between the image of the back of the playing card based on the image data and the reference data is identified in b) by an alphanumeric rating, color rating or symbolic rating. The sensor may be located at a position elevated above a surface of the gaming table. For example, the sensor may be elevated to a height wherein infrared radiation reflected from the back surface of the playing card at an angle of between 60 and 90 degrees from horizontal is received by the sensor. This can be done within a housing or on a casino floor where the sensor is housed within a dome secured to a ceiling.

In a preferred method and system, in addition to the infrared radiation, the method contemporaneously (in an adjacent time frame, an overlapping time frame or the same time frame) provides ambient ultraviolet radiation at the gaming table or in a housing and reflecting at least some of that ultraviolet radiation off the back surface of the playing card; capturing reflected ultraviolet radiation with an ultraviolet radiation sensor; the ultraviolet radiation sensor transmitting signals based on the reflected ultraviolet radiation captured by the ultraviolet radiation sensor; the transmitted signals based on the ultraviolet radiation providing data that contains image data of the back of the playing card; and displaying an image of the back of the playing card based on the ultraviolet image data. A processor may combine the infrared and ultraviolet image data to form a single composite image of the back of the playing card. The provided ambient infrared radiation may be pulsed at the back of the playing card to reduce infrared heating of the back of the playing card.

The invention may also include a system for detecting errors in the back of playing cards comprising:
  an ambient infrared radiation source for directing infrared radiation at a surface;
  an infrared radiation sensor for capturing reflected ambient infrared radiation;
  the infrared radiation sensor configured to transmit signals based on captured reflected infrared radiation;
  the transmitted signals providing data that contains image data reflected off of the surface;
  a processor configured to receive the transmitted signals, process the transmitted signals and transmit the processed transmitted signals in a format that can be displayed on a display system; and
  a display system configured to display an image of the surface from which infrared radiation was reflected based on the image data.

The surface in the system preferably comprises a playing card, with a back surface of the playing card without (intentional) suit and rank information printed thereon. By lack of intent is meant that an "honest" card is used where the backs and sides of the individual cards are intended to be indistinguishable from one another. There may be fraudulent or illegal markings or printing defects that can distinguish between cards and provide or suggest face values, suits and/or ranks of the playing cards. It is an aspect of the present technology to detect such fraudulent, criminal or accidental face (value, suit and/or rank) identifying markings on the back side of the playing cards. In some cases, the printing errors may be as subtle as smears, disorientations, poor ink transfers, misalignment, lack of color registration, or ink bleed (horizontal or through the thickness of the cards). These honest defects are still sources of player advantage outside the scope of the rules of game play and would be used by a player seeking an advantage, whether that player believes the use is ethical or not.

Spurious or intentional markings can be the result of fraudulently intended transfer of markings of any sort to give a player an advantage. The markings may be subtle visible markings (as an obvious marking would be seen by all and call attention to the fact that there has been marking) such as minute cuts on edges (which might be more easily felt than seen), infrared radiation reflecting inks or pigments, ultraviolet radiation reflecting inks or pigments, surface abrading steps that can alter the radiation reflecting properties of the back surface of the playing card, and any other marking that can be visually detected. The visual detection may be enhanced or enabled by lenses or glasses that aid in the reading of the otherwise invisible inks. As the player that has marked the cards will be reading through glasses from the reflection of truly ambient radiation and not intentionally projected radiation (it would be difficult to provide projected radiation unless there were cooperation from the casino or structure where the card game was being played).

By providing a potentially full range of spectral illumination (infrared, ultraviolet and even additional visible white light illumination) on the backs of the playing cards, detection of all forms of image marking is enabled. As players who are seeking information from such markings will typically have to use only the available background radiation for viewing (since a player shining a light onto the playing cards would be easily detected), the use of additional casino controlled projection of radiation enables greater image content and intensity availability for security purposes in detecting flaws and markings. Reflected radiation is collected by a sensor positioned to be within a range of reflected radiation from the surface of playing cards. Using standard software for image capture (as known in the art cited herein), the collected radiation is converted to image data which is transmitted to an image display system to create the displayed image. This transformation of the raw received radiation could be performed by local logic (e.g., field programmable gated arrays, ASICs, chip boards and the like) or by a dedicated or local processor in communication with the system. In one simple embodiment, a single box or housing (usually with a top, bottom, two sides and a back, with the front open to allow insertion of the playing cards, as in FIG. 1) may have multiple infrared emitters (LEDs, lasers, bulbs, semiconductors, etc.), multiple ultraviolet radiation emitters (LEDs, bulbs, semiconductors, lasers, etc.) and even white visible light emitters within the housing direct the radiation at an area on the bottom of the box where one or more playing cards can be placed, backside (no card symbols shown) facing upwards. The sensors would be placed at a location (e.g., facing downward from the inside top of the housing) to most efficiently collect the reflected radiation. The sensor or camera should extend to a position at least as low as the lowest emitter, and preferably lower than the lowest emitter so as to minimize direct transmission of the radiation from the emitters to the sensor, without reflection. There should be at least two emitters for each of the infrared and ultraviolet portions of the spectrum to assure broad coverage of the surface of the playing cards, even though a single emitter for each portion of the spectrum would work. For the infrared, the spectral range may, by way of non-limiting examples, be within 780-1100 nm, the ultraviolet may be within 280-410 nm and the like. There may be 1, 2, 3, 4, 5, 6 or more emitters for each spectral range, as the power consumption for each wavelength can be quite small. The low power consumption would allow for portable battery powered units as well as power cord plug-in units.

FIG. 1 shows a full frontal view of a box construction 2 for the system. This box construction 2 could also be sized to be a section within a delivery shoe or playing card shuffler (neither shown). The box construction 2 has a top 4, A BOTTOM 6, A LEFT SIDE 8 AND A RIGHT SIDE 10. One or more playing cards 12a and 12b may lie on the bottom 6 of the box construction 2. A series of infrared emitters (triangles 14) and ultraviolet emitters (squares 16) are shown distributed along the lower inside surface of the top 4. A camera/sensor box (with sensing capability matching or including the output of emitters 14 and 16) extends below the farthest extension of the emitters 14 and 16. A signal conducting system (20) such as wires, plates, panels and the like carries signals between components. An I/O port to carry signals to a processor or logic system (not shown) is in communication with the signal conducting system (20).

The original signals (reflected radiation) captured by the sensors is then converted to data that can be displayed (or even just analyzed by a processor configured with software). An aspect of the technology can be to merely display an image of the back of the playing card(s) so that markings can be visually inspected for, or to have the captured image of the back of the card visually or processor compared with a stored image of the back of that format of playing card. These stored images can either be within a look-up table of a large number of playing cards, or one or more images (to provide a standard image) can be made of the backs of playing cards at the beginning of a session to create an comparison image for that card set. A "standard" image of the back of playing cards can be important where manufacturing defects might be present. Slight rotations of the printed images, smears, discolorations, poor inking and the like can be as effective readable markings for individual playing cards as intentionally applied markings or daubs.

Edge markings and edge cuts can also be detected by software looking for variations in the linearity of sides or edges of playing cards. Surface abrasions of the backs of the cards (which would not require ink or pigments applied) would alter the reflection characteristics in areas of the cards which could be visually or tactilely detected (with or without a player using artificial means) and could be detected by software looking for deviations in ideal reflection off the backs of the playing cards.

The system my further have: an ambient ultraviolet radiation source for directing ultraviolet radiation at the surface; an ultraviolet radiation sensor for capturing reflected ambient ultraviolet radiation; the ultraviolet radiation sensor configured to transmit signals based on captured reflected ultraviolet radiation; the transmitted signals from the ultraviolet radiation symbol providing data that contains ultraviolet image data reflected off of the surface; a processor configured to receive the transmitted signals from the reflected ultraviolet radiation, process the transmitted signals from the reflected ultraviolet radiation and transmit the processed transmitted signals from the reflected ultraviolet radiation in a format that can be displayed on a display system; and a display system configured to display an image of the surface from which ultraviolet radiation was reflected based on the infrared image data and the ultraviolet radiation data. Again, the infrared radiation source is pulsed to reduce heating of the surface by infrared radiation. The infrared radiation source may be configured to pulse the infrared radiation contemporaneously with the emitting of ultraviolet radiation by the ultraviolet radiation source. The processor may be configured to combine the infrared radiation signals and the ultraviolet radiation signals to form a composite image on the display system. The processor may be configured to compare that transmitted signals with reference data of a standard playing card back. The processor may be configured to i) compare the transmitted signals comprising image data of the back of a playing card based on reflected data and reference data stored in memory of a standard playing card back surface and ii) identify differences between the transmitted signals comprising image data of the back of a playing card based on reflected data and reference data stored in memory and the processor then is configured to provide image data of the comparison to either a) highlighted in a visual display or b) the processor identifying a degree of difference between the image of the back of the playing card based on the image data and the reference data, and the processor may be configured to determine a degree of difference between the image of the back of the playing card based on the image data and the reference data is identified in b) by an alphanumeric rating, color rating or symbolic rating. Again, the infrared sensor may be located at a position elevated above a surface of the gaming table, especially where the sensor is at a position elevated to a height wherein infrared radiation reflected from the back surface of the playing card at an angle of between 60 and 90 degrees from horizontal is received by the sensor. The processor may be configured to i) compare the combined transmitted signals comprising image data of the back of a playing card based on reflected data and reference data stored in memory of a standard playing card back surface and ii) identify differences between the combined transmitted signals comprising image data of the back of a playing card based on reflected data and reference data stored in memory and the processor then is configured to provide image data of the comparison to either a) highlighted in a visual display or b) the processor identifying a degree of difference between the image of the back of the playing card based on the image data and the reference data, and again the processor may be configured to determine a degree of difference between the image of the back of the playing card based on the image data and the reference data is identified in b) by an alphanumeric rating, color rating or symbolic rating. The infrared sensor is located at a position elevated above a surface of the gaming table, such as where the surface is provided within a housing comprising a bottom, a top, a back and two sides, and the ambient source of infrared radiation is provided by at least two infrared emitters on the top, back and/or two sides, and the infrared sensor is supported on the top. The surface may be provided within a housing comprising a bottom, a top, a back and two sides, and the ambient source of infrared radiation is provided by at least two infrared emitters on the top, back and/or two sides, and the ambient source of ultraviolet radiation is provided by at least two ultraviolet emitters on the top, back and/or two sides, and the infrared sensor and the ultraviolet sensor are supported on the top. The housing may include a card support for a set of playing cards, and a moving system for moving individual playing cards from the card support to the surface so that a back of the playing card is exposed to the transmitted infrared radiation and infrared radiation is reflected from the back of the playing card. This housing may be a mechanical or manual shoe, a shuffling or randomization system.

It is also to be noted that the system of the present technology may be used to verify other gaming objects to prevent fraudulent substitution of gaming objects. Invisible dyes (again IR or UV visible) can be embedded in or painted on (with readable codes), and the system can be used to verify the chips based on reading the applied code. To prevent duplication of the code by third parties, the code can be altered easily by regular removal (a simple wash) and reapplication of the invisible code. Chips may be easily coated on a regular basis, but die would usually have to have the ink or pigment embedded within the structure to be viewed by the system technology, with UV and/or IR radiation and reflection. This system enables more secure and faster verification of dice then the standard visual inspection. The identical system, with only software varied to address dice image or chip image content can be used.

Although specific structures, components, materials, dimensions and parameters have been described to assure enablement of the invention, those are merely specific examples within the generic concepts of the present invention and should not be read as limiting the scope of the invention as claimed.

What is claimed:

1. A method for detecting errors in the back of playing cards within a housed system having two inner side surfaces, an inner back surface, an inner top surface, an inner bottom surface and an open front area through which playing cards may be manually placed and removed, the method comprising:
    placing a playing card through the front area face-down onto the inner bottom surface of the housed system;
    providing ambient infrared radiation from the inner top surface of the housed system and reflecting at least some of that infrared radiation off a back surface of a playing card to an infrared radiation sensor at the inner top surface within the housed system;
    capturing reflected infrared radiation with the infrared radiation sensor at the inner top surface within the housed system;
    the infrared radiation sensor transmitting signals based on the reflected infrared radiation captured by the infrared radiation sensor;
    the transmitted signals providing data that contains image data of the back of the playing card; and
    displaying an actual image of the back of the playing card that includes erroneous markings or fraudulently applied markings indicating at least rank of the playing card based on the fraudulently applied markings within the image data.

2. The method of claim 1 wherein the sensor is located at a position elevated above a surface of the playing card and attached to the inner top surface of the housed system.

3. The method of claim 2 wherein the sensor is elevated to a height wherein infrared radiation reflected from the back surface of the playing card at an angle of between 60 and 90 degrees from horizontal is received by the sensor.

4. The method of claim 1 wherein in addition to the infrared radiation, the method contemporaneously:
    providing ambient ultraviolet radiation at the gaming table and reflecting at least some of that ultraviolet radiation off the back surface of the playing card;
    capturing reflected ultraviolet radiation with an ultraviolet radiation sensor;
    the ultraviolet radiation sensor transmitting signals based on the reflected ultraviolet radiation captured by the ultraviolet radiation sensor;
    the transmitted signals based on the ultraviolet radiation providing data that contains image data of the back of the playing card; and
    displaying an actual image of the back of the playing card based on the provided ultraviolet image data.

5. The method of claim 4 wherein a processor combined the infrared and ultraviolet image data to form a single composite image of the back of the playing card that includes the fraudulently applied markings.

6. The method of claim 1 wherein the provided ambient infrared radiation is pulsed at the back of the playing card to reduce infrared heating of the back of the playing card.

7. The method of claim 4 wherein the provided ambient infrared radiation is pulsed at the back of the playing card to reduce infrared heating of the back of the playing card and the fraudulent markings were manually applied.

8. A system for detecting errors in the back of playing cards within a housed system having two inner side surfaces, an inner back surface, an inner top surface, an inner bottom surface and an open front area through which playing cards may be manually placed and removed, the system comprising:
    an ambient infrared radiation source for directing infrared radiation at a surface on the inner top surface;
    an infrared radiation sensor on the inner top surface for capturing reflected ambient infrared radiation from the inner bottom surface;

the infrared radiation sensor configured to transmit signals based on captured reflected infrared radiation;

the transmitted signals providing data that contains image data reflected off of the surface comprising erroneous markings or fraudulent markings on a back surface on the back of the playing card;

a processor configured to receive the transmitted signals, process the transmitted signals and transmit the processed transmitted signals in a format that can be displayed on a display system; and a display system configured to display an actual image of the surface from which infrared radiation was reflected based on the image data including image data indicating the erroneous or fraudulent markings on the back surface of the playing card.

9. The system of claim 8 wherein the surface comprises a playing card, with a back surface of the playing card without suit and rank information printed thereon but containing erroneous markings or fraudulently applied markings, and the display system is configured to display the erroneous markings or fraudulently applied markings.

10. The system of claim 8 further comprising:
an ambient ultraviolet radiation source for directing ultraviolet radiation at the surface;
an ultraviolet radiation sensor for capturing reflected ambient ultraviolet radiation;
the ultraviolet radiation sensor configured to transmit signals based on captured reflected ultraviolet radiation;
the transmitted signals from the ultraviolet radiation symbol providing data that contain ultraviolet image data reflected off of the surface;
a processor configured to receive the transmitted signals from the reflected ultraviolet radiation, process the transmitted signals from the reflected ultraviolet radiation and transmit the processed transmitted signals from the reflected ultraviolet radiation in a format that can be displayed on a display system; and
a display system configured to display an image of the surface from which ultraviolet radiation was reflected including the erroneous markings or fraudulent markings based on the infrared image data and the ultraviolet radiation data.

11. The system of claim 10 wherein the infrared radiation source is pulsed to reduce heating of the surface by infrared radiation.

12. The system of claim 11 wherein the infrared radiation source is configured to pulse the infrared radiation contemporaneously with the emitting of ultraviolet radiation by the ultraviolet radiation source.

13. The system of claim 12 wherein the processor is configured to combine the infrared radiation signals and the ultraviolet radiation signals to form a composite image on the display system.

14. The system of claim 8 wherein the surface is provided within a housing comprising a bottom inner surface, a top inner surface, a back and two inner side surfaces, and the ambient source of infrared radiation is provided by at least two infrared emitters on the top inner surfaces, back and/or two inner sides, and the infrared sensor is supported on the top inner surface.

15. The system of claim 10 wherein the surface is provided within a housing comprising an inner bottom surface, a top inner surface, a back inner surface and two inner side surfaces, and the ambient source of infrared radiation is provided by at least two infrared emitters on the top, back and/or two sides, and the ambient source of ultraviolet radiation is provided by at least two ultraviolet emitters on the top inner surface, back and/or two inner side surfaces, and the infrared sensor and the ultraviolet sensor are supported on the top inner surface.

16. The system of claim 14 wherein the housing includes a card support for a set of playing cards, and a moving system for moving individual playing cards within the housing from the card support to the surface within the housing so that a back of the playing card is exposed to the transmitted infrared radiation and infrared radiation is reflected from the back of the playing card within the housing.

17. The system of claim 15 wherein the housing includes a card support for a set of playing cards, and a moving system for moving individual playing cards from the card support to the surface within the housing so that a back of the playing card is exposed to the transmitted infrared radiation and ultraviolet radiation and infrared radiation within the housing and ultraviolet radiation are reflected from the back of the playing card within the housing.

18. A system for detecting errors in the back of playing cards comprising:
a housing with a base for supporting a playing card;
the housing having a front that is open to allow both insertion and removal of the playing cards to the base under a top surface inner support within the housing;
an ambient infrared radiation source on the top surface inner support for directing infrared radiation at a surface of the base supporting a playing card and at least one other radiation emitter on the top surface inner support selected from ultraviolet radiation emitters and visible radiation emitters;
an infrared radiation sensor on the top surface inner support for capturing reflected ambient infrared radiation and a radiation sensor on the top surface inner support for the at least one other radiation emitter;
the infrared radiation sensor and the at least one other radiation sensor configured to transmit signals based on captured reflected infrared radiation;
the transmitted signals providing data that contains image data reflected off of the surface either simultaneously or in sequence;
a processor configured to receive the transmitted signals, process the transmitted signals and transmit the processed transmitted signals in a visual image format that can be displayed on a display system; and
a display system configured to display an actual image of the surface from which infrared radiation was reflected based on the image data.

19. The system of claim 18 wherein there are three radiation emitters comprising a first ambient infrared radiation source for directing infrared radiation at a surface, a second ambient ultraviolet radiation emitter and a third ambient visible radiation emitter.

20. The system of claim 19 wherein a control panel allows for independent control of output from each of the three radiation emitters.

* * * * *